United States Patent
Kupracz et al.

(10) Patent No.: US 12,145,130 B2
(45) Date of Patent: Nov. 19, 2024

(54) MULTIMODAL ADSORPTION MEDIUM WITH MULTIMODAL LIGANDS, METHOD FOR THE PREPARATION AND USE THEREOF

(71) Applicant: Sartorius Stedim Biotech GmbH, Göttingen (DE)

(72) Inventors: Lukas Kupracz, Hannover (DE); Florian Taft, Hannover (DE); Louis Villain, Hannover (DE); Kornelia Kuper, Göttingen (DE)

(73) Assignee: Sartorius Stedim Biotech GmbH, Göttingen (DE)

( * ) Notice: Subject to any disclaimer, the term of this patent is extended or adjusted under 35 U.S.C. 154(b) by 291 days.

(21) Appl. No.: 17/465,052

(22) Filed: Sep. 2, 2021

(65) Prior Publication Data
US 2022/0055015 A1 Feb. 24, 2022

Related U.S. Application Data

(63) Continuation of application No. 16/092,353, filed as application No. PCT/EP2017/000430 on Apr. 5, 2017, now abandoned.

(30) Foreign Application Priority Data

Apr. 12, 2016 (DE) .................. 10 2016 004 432.2

(51) Int. Cl.
| | | |
|---|---|---|
| *B01D 15/38* | (2006.01) | |
| *B01J 20/24* | (2006.01) | |
| *B01J 20/26* | (2006.01) | |
| *B01J 20/288* | (2006.01) | |
| *B01J 20/289* | (2006.01) | |
| *B01J 20/32* | (2006.01) | |
| *C07K 1/16* | (2006.01) | |
| *C07K 16/00* | (2006.01) | |

(52) U.S. Cl.
CPC ........ *B01J 20/288* (2013.01); *B01D 15/3847* (2013.01); *B01J 20/24* (2013.01); *B01J 20/261* (2013.01); *B01J 20/265* (2013.01); *B01J 20/289* (2013.01); *B01J 20/3212* (2013.01); *B01J 20/3219* (2013.01); *B01J 20/3227* (2013.01); *B01J 20/3248* (2013.01); *B01J 20/3285* (2013.01); *C07K 1/16* (2013.01); *C07K 1/165* (2013.01); *C07K 16/00* (2013.01); *B01J 2220/52* (2013.01)

(58) Field of Classification Search
CPC .. B01J 20/3227; B01J 20/3285; B01J 20/288; B01J 20/261; B01J 20/265; B01J 20/289; B01J 20/3248; B01J 20/24; B01J 20/3219; B01J 20/3212; B01J 2220/52; B01D 15/3847; C07K 16/00; C07K 1/16; C07K 1/165

See application file for complete search history.

(56) References Cited

U.S. PATENT DOCUMENTS

| | | |
|---|---|---|
| 3,951,815 A | 4/1976 | Wrasidlo |
| 5,431,807 A | 7/1995 | Frechet et al. |
| 6,852,230 B2 | 2/2005 | Belew et al. |
| 7,772,382 B2 | 8/2010 | Okamoto |
| 8,017,740 B2 | 9/2011 | Gagnon |
| 8,182,679 B2 | 5/2012 | Liu et al. |
| 8,877,904 B2 | 11/2014 | Gagnon et al. |
| 2010/0210821 A1 | 8/2010 | Gilljam et al. |
| 2012/0202976 A1 | 8/2012 | Axen et al. |
| 2013/0109807 A1 | 5/2013 | Gagnon |
| 2014/0370614 A1 | 12/2014 | Liu et al. |

FOREIGN PATENT DOCUMENTS

| | | |
|---|---|---|
| CN | 109070051 | 12/2018 |
| DE | 102016004432 | 10/2017 |
| EP | 0316492 | 5/1989 |
| EP | 0665867 | 1/1998 |
| EP | 3442700 | 5/2020 |
| GB | 2232984 | 1/1991 |
| JP | S6348453 W | 3/1988 |
| JP | H01169355 | 7/1989 |
| JP | 2007145743 | 6/2007 |
| JP | 2008528966 | 7/2008 |
| JP | 2014522479 | 9/2014 |
| JP | 2019513549 | 5/2019 |
| WO | WO2002/005959 | 1/2002 |
| WO | WO2005/082483 | 9/2005 |
| WO | WO2006/081002 | 8/2006 |
| WO | WO2012/151352 | 11/2012 |

OTHER PUBLICATIONS

Chaikittisilp et al. Poly(allylamine)Mesoporous Silica Composite Materials for CO2 Capture from Simulated Flue Gas or Ambient Air. IInd. Eng. Chem. Res. 2011, 50, 14203-14210 (Year: 2011).*

(Continued)

*Primary Examiner* — Shafiqul Haq
(74) *Attorney, Agent, or Firm* — Klarquist Sparkman, LLP

(57) ABSTRACT

The present invention relates to a multimodal adsorption medium, in particular a multimodal chromatography medium, a method for its production, as well as use of the adsorption medium according to the invention or an adsorption medium produced according to the invention for the purification of biomolecules.

6 Claims, 2 Drawing Sheets

(56) References Cited

OTHER PUBLICATIONS

Dutta et al., "Multifaceted development and application of biopolymers for biology, biomedicine and nanotechnology," *Advances in Polymer Science* 254:1-346, 2013 (Oct. 7, 2013).
International Search Report and Written Opinion for PCT/EP2017/000430 (mailed Oct. 19, 2017) (w/English International Search Report).
Li et al., "Study of dual responsive poly[(maleilated dextran)-graft-N-isopropylacrylamide)] hydrogel nanoparticles: preparation, characterization and biological evaluation," *Polymer International* 58:1023-1033, 2009 (Sep. 1, 2009).
Office Action for Japanese Application No. 2018-553089, mailed Nov. 26, 2019 (w/English translation).

* cited by examiner

MULTIMODAL ADSORPTION MEDIUM WITH MULTIMODAL LIGANDS, METHOD FOR THE PREPARATION AND USE THEREOF

This is a continuation of U.S. patent application Ser. No. 16/092,353, filed Oct. 9, 2018, which is the U.S. National Stage of International Application No. PCT/EP2017/000430, filed Apr. 5, 2017, which in turn claims the benefit of German Application No. 10 2016 004 432.2, filed Apr. 12, 2016, both of which are incorporated herein by reference in their entireties.

The present invention relates to a multimodal adsorption medium, in particular a multimodal chromatography medium, a method for its production, and use of the adsorption medium according to the invention or an adsorption medium produced according to the invention for the purification of biomolecules.

DETAILED DESCRIPTION

Figure 1:
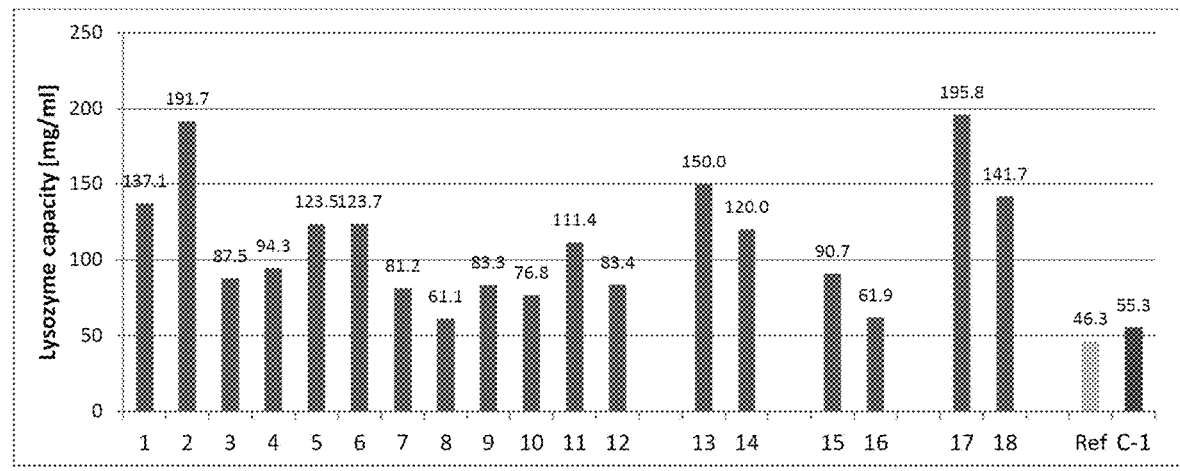
FIG. 1 shows the binding capacity to lysozyme for examples 1 to 18, for comparison example 1 (C-1), and for the strong cation exchanger-membrane absorber Sartobind S (Ref) known in the prior art.

The term "adsorption medium" refers to adsorbents that have functional surface groups, also referred to in the following as "ligands" and/or "chromatographically active centers," which can selectively form bonds with specified components of fluids. According to the invention, target substance(s) and/or contaminant(s) are referred to as "adsorbates," wherein this can also refer to a plurality of different substances.

Adsorbates can be individual molecules, associations, or particles, wherein these are preferably proteins or other substances of biological origin.

The binding of the adsorbates to the adsorbent can be reversible or irreversible, and in any case, it allows them to be separated from the fluids, which for example can be aqueous liquids and are referred to in the following as "media." Desorption and the accompanying rinsing steps, etc., are combined under the term "elution" and the medium used for elution is the "eluent." The components may be one or a plurality of target substances and/or one or a plurality of contaminants. "Target substances" are valuable substances that are to be obtained from the medium in enriched or pure form. For example, target substances can be recombinant proteins such as monoclonal antibodies. "Contaminants" are substances whose absence or removal from the fluid is required or desirable for technical, regulatory, or other reasons. For example, contaminants can be viruses, proteins, amino acids, nucleic acids, endotoxins, protein aggregates, ligands or parts thereof. In order to remove contaminants, a process referred to as "negative adsorption," adsorption can (may) be carried out irreversibly if the adsorbent is only to be used once. In adsorption of the target substance(s), the process must be carried out reversibly. One can carry out either simple enrichment or separation into multiple target substances, wherein in the latter case, adsorption, desorption or both can take place selectively.

This process is referred to as adsorptive substance separation or chromatography. Conventional adsorbents for chromatography are either particulate and are used in columns in the form of packings, or are in the form of adsorption membranes, which are usually located in modules having designs corresponding to those commonly used in membrane filtration (e.g. wound module, stack module, etc.). The requirement for non-specific adsorption that is as low as possible is ordinarily common to all adsorbents.

Numerous synthetic and natural ligands are known in the prior art. Binding of the ligand to the carrier can be preceded by "activation" of the carrier, i.e. the introduction of reactive functional groups capable of spontaneously binding the ligand. More rarely, the ligand itself has a reactive group, with an example being the reactive dyes used as dye ligands in the textile industry. Methods for the binding of functional groups are known per se to the person skilled in the art (e.g. Greg T. Hermanson, A. Krishna Mallia, Paul K. Smith, Immobilized Affinity Ligand Techniques, Academic Press, Inc., 1992).

The filtration, purification or removal of biomolecules such as proteins, amino acids, nucleic acids, viruses or endotoxins from liquid media is of great importance for the biopharmaceutical industry. Most of the applications in contaminant removal currently use conventional chromatography gels or chromatography membranes.

Ion-exchange chromatography has also taken on a position of importance in the purification of biomolecules. Cation exchangers comprising mixed-mode or multimodal ligands have long been known in the prior art. For example, U.S. Pat. No. 5,431,807 A discloses a multimodal chromatographic separation medium in which hydrophobic ligands such as benzyl ligands are fixed in pores of a first size range, while ion-exchanging ligands are fixed in pores of a second size range spatially separated from the hydrophobic ligands. Similarly, EP 0665867 B1 describes a method for pore-size-selective chemical modification of porous materials wherein for example hydrophobic ligands are fixed in pores of a first size range, while cation-exchanging ligands are fixed in pores of a second size range spatially separated from the hydrophobic ligands. US 2012/0202976 A1 discloses a chromatographic separation medium in which both a first type of hydrophobic ligand and a second type of ion-exchanging ligand are bound to the chromatography matrix, the latter via so-called extenders. In these systems, the different functional groups are consequently present in different molecular chains and are spatially separated.

A drawback of known cation exchangers is that they can undergo binding only with substances having relatively low ionic strengths, so that the medium must often be diluted before adsorption. The known adsorption media therefore do not tolerate high salt concentrations in binding of substances, thus requiring an additional dilution step and large fluid volumes in correspondingly large-scale chromatography facilities.

In U.S. Pat. No. 8,877,904 B2, chromatography matrices are disclosed on which multimodal ligands with cation-exchanging and hydrophobic functional groups are fixed, wherein for example ligands are bound to the surfaces of a carrier material starting from phenylalanine or 6-aminohexanoic acid. U.S. Pat. No. 8,017,740 B2 discloses chromatography matrices based on porous molded bodies, preferably derived from inorganic hydroxy- or fluorapatites on which both hydrophobic and cation-exchanging ligands are fixed, wherein for example Capto™ MMC, a so-called "mixed mode" ligand, is mentioned. Chromatography matrices comparable to this Capto™ MMC ligand are also disclosed in US 2013/0109807 A1. The Capto™ MMC ligand comprises a 2-benzoylaminobutanoic acid residue, which is obtained by reaction of homocysteine thiolactone with benzoyl chloride and subsequent thiolactone opening. Binding of the Capto™ MMC ligand to the stationary phase then takes place via the thiol group by means of nucleophilic substitution or ring opening.

U.S. Pat. No. 6,852,230 B2 discloses chromatography matrices comprising ligands with cation-exchanging and hydrophobic groups, wherein the matrices allow a high recovery rate of bovine serum albumin at high salt concentrations. These multimodal systems are described in greater detail in the relevant publication, B.-L. Johansson et al., Journal of Chromatography A, 1016 (2003), 35-49, wherein ligands are immobilized on activated Sepharose™ 6 Fast Flow by means of two variants. In a multistep synthesis process, mercaptopropionic acid is first bound to the activated carrier. The acid functional group is then activated with dicyclohexylcarbodiimide (DCC) and N-hydroxysuccinimide (NHS), and the resulting ester is finally reacted with an amino acid derivative in order to introduce a corresponding cation-exchanging functionality.

The result for the systems known in the prior art is that their production generally comprises complex steps, namely:
i) Bringing of a reactive group onto a chromatographic carrier and optimum activation thereof.
ii) Reaction of the modified carrier thus produced with a thiol compound containing an acid functional group.
iii) Activation of the acid functional group of the sold carrier with a suitable reagent (e.g. N-hydroxysuccinimide (NHS)) in the presence of dicyclohexylcarbodiimide (DCC)) in an organic solvent.
iv) Addition of an amino acid derivative that comprises residue R, suitable for producing a complete ligand that is bound to a carrier.

For example, a synthesis method for Capto™ MMC matrices of prior art comprises in step i) the reaction of e.g. Sepharose with allyl glycidyl ether and the subsequent activation of the resulting product with bromine, followed in step ii) by reaction with a thiolactone.

In this method, the reaction of the last step in particular does not take place completely, with the result that a product actually having two different ligands is always obtained, which contains a thioether linker containing an acid functional group and resulting from an unsuccessful reaction in step (iii) or (iv), and the desired end product. A chromatographic carrier composed of a mixture of two different ligands can cause multiple problems if it is used in a separation method. As the ratio of the various ligands can fluctuate from batch to batch, the chromatography media produced in this manner possess different properties depending on the batch, so that separation methods that have been developed are not reproducible when the batch is changed. Moreover, use of different separate ligands can result in the drawback of non-homogeneous distribution of the different ligands on the chromatography medium.

Another problem associated with the above-described conventional methods is that it is often impossible to obtain a sufficiently high ligand density, which is detrimental in particular to the binding capacity of small proteins. This problem can at least partially be solved using polymeric spacers, which are fixed on the surface of the chromatography matrix and via which additional ligands can be bound to the matrix.

The object of the invention is therefore to provide an adsorption medium that can be simply and reproducibly produced and should have a high binding capacity that can be selectively adjusted over a broad salt concentration range.

This object is achieved by the embodiments of the present invention characterized in the claims.

In particular, according to the invention, a multimodal adsorption medium is provided, in particular a multimodal chromatography medium, comprising a polymeric carrier material C to which multimodal ligands of the following structure -G-$(CO_2H)_n$ are covalently bonded via an —X—(C=O) group:

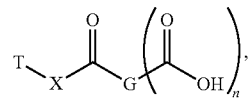

wherein X denotes —NR—, —O— or —S— and R denotes alkyl, alkenyl, aryl, heteroaryl or hydrogen, G denotes a group selected from the group composed of a branched or unbranched $C_{2-20}$ alkyl group that can contain one or a plurality of heteroatoms selected from O, S, N and halogens, and optionally at least one aromatic substituent, a substituted or unsubstituted $C_{3-10}$ cycloalkyl group that can contain one or a plurality of heteroatoms selected from O, S, N and halogens, and optionally at least one aromatic substituent, a branched or unbranched $C_{2-20}$ alkenyl group that can contain one or a plurality of heteroatoms selected from O, S, N and halogens, and optionally at least one aromatic substituent, a substituted or unsubstituted $C_{6-20}$ aryl group that can contain one or a plurality of heteroatoms selected from O, S, N and halogens, and a substituted or unsubstituted $C_{4-20}$ heteroaryl group that can contain one or a plurality of heteroatoms selected from O, S, N and halogens, wherein n is a whole number that is 1 or higher.

In a preferred embodiment of the multimodal adsorption medium, the G group is selected from the group composed of a branched or unbranched $C_{4-20}$ alkyl group that can contain one or a plurality of heteroatoms selected from O, S, N and halogens, and optionally at least one aromatic substituent, and a branched or unbranched $C_{3-20}$ alkenyl group that can contain one or a plurality of heteroatoms selected from O, S, N and halogens, and optionally at least one aromatic substituent.

Within the meaning of the present invention, the term "multimodal" is understood to mean that the ligands comprise two or more different functional groups, which thus undergo interactions with the target molecules based on different chemical mechanisms, so that the latter are bound to the adsorption medium. According to the invention, the multimodal adsorption medium or the multimodal ligands comprise at least cation-exchanging acidic groups and simultaneously hydrophobic groups. By selection of the hydrophobic G group, further functional groups can also be integrated that undergo further interactions with the target substances, such as thiophilic interactions, π-π-interactions, ion exchange interactions or hydrogen bridge bonds.

Preferably, the adsorption medium according to the invention comprises only one type of multimodal ligand, which means that only identical ligands of the above structure are bound to the polymeric carrier material. Because the multimodal ligand structure is produced using only one reagent, as will be described in further detail below, the ratio of carboxylic acid groups to G groups, which allow further interactions, remains constant on the adsorption medium according to the invention. For this reason, in contrast to a modification method with two different ligands or incomplete reactions, the result of the production process is always reproducible.

In a particularly preferred embodiment of the adsorption medium according to the invention, the G group is a hydrophobic group that can bind to the target substances via Van der Waals or π-π-interactions.

The production of the adsorption medium according to the invention is based on a novel modification protocol in which a polymeric carrier material with at least one —XH group, where X=—NR—, —O— or —S— and R=alkyl, alkenyl, aryl, heteroaryl or H, is used as a starting material that is reactive with carboxylic acid derivatives while forming a covalent bond —X—(C=O). The —XH groups are reacted with a ligand precursor so that the resulting ligands are bound to the carrier material via a covalent bond —X—(C=O) and each have at least one free carboxylic acid group. Preferably, the —XH groups are functionalized with carboxylic anhydrides, as can be illustrated by means of the following diagram:

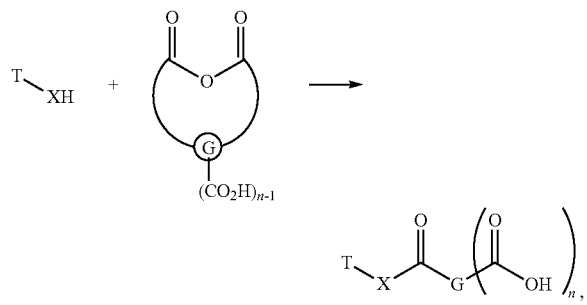

wherein X, G and n are as defined above. In the G groups, which themselves have no carboxylic acid groups —COOH as substituents, the only carboxylic acid group present in the ligand G-$(CO_2H)_n$ results from the ring-opening reaction of the carboxylic anhydride with the nucleophilic group —XH, and n is equal to 1.

In the G groups, which themselves have at least one carboxylic acid group —COOH as a substituent, n is greater than or equal to 2, wherein one of the carboxylic acid groups results from the ring-opening reaction of the carboxylic anhydride with the nucleophilic group —XH.

Particularly preferably, the G groups are hydrophobic groups.

According to an embodiment of the present invention, the group —X—(C=O) is —NH—(C=O). This means that the group —XH is a primary amino group, so that the resulting -G-$(CO_2H)_n$ ligands are bound to the carrier material via a secondary amide bond —NH—(C=O).

According to the invention, any material that is suitable for chromatographic processes as a carrier material of the stationary phase is suitable as a polymeric carrier material. There are no particular limitations on the polymeric carrier material, which can also be referred to a chromatography matrix, provided that is has on its surface —XH groups, where X=—NR—, —O— or —S— and R=alkyl, alkenyl, aryl, heteroaryl or H, to which the multimodal ligands can bind or be bound. These groups can already be present on the surface of the carrier material or can be introduced in a suitable manner. According to the invention, therefore, one can either use a polymeric carrier material that originally comprises functional groups (such as polyester fibers), or a polymeric carrier material into which suitable functional groups can be introduced by means of a surface modification known to the person skilled in the art. In this connection, examples of known surface modifications include substitution and addition reactions, reaction with functional epoxides, activated acids or active esters, activation by means of plasma treatment, e-beam (electron beam treatment), gamma irradiation, coating, hydrolysis, aminolysis, oxidation, reduction, reaction with functional carbenes and/or nitrenes, etc.

According to an embodiment of the present invention, the polymeric carrier material comprises at least one material selected from the group composed of natural or synthetic fibers, (polymer) membranes, porous, polymeric monolithic molded bodies, polymer gels, films, nonwovens and wovens.

Examples of natural or synthetic fibers that can be used as a material for the polymeric carrier material of the adsorption medium according to the invention include polyester fibers (such as "Winged Fibers" from the firm Allasso Industries, composed of polyethylene terephthalate (PET) or "4DG™ Fibers" from the firm Fiber Innovation Technology, composed of polyethylene terephthalate) and fibers comprising cellulose, cellulose derivatives, Nylon, polyethylene (PE), polyamide (PA), sulfone (PES), polyvinylidene difluoride (PVDF), polytetrafluoroethylene (PTFE), polypropylene (PP) and polysulfone as a structuring component, wherein the materials can be used individually or in corresponding combinations. Preferably, polyester fibers, in particular fibers composed of polyethylene terephthalate or polybutylene terephthalate (PBT) and polyamide fibers are used.

Examples of (polymer) membranes that can be used as a material for the polymeric carrier material of the adsorption medium according to the invention include membranes comprising cellulose, cellulose derivatives, Nylon, polyester, polyethylene (PE), polyamide (PA), sulfone (PES), polyvinylidene difluoride (PVDF), polytetrafluoroethylene (PTFE), polypropylene (PP) and polysulfone as a structuring component, wherein the materials can be used individually or in corresponding combinations. Preferably, membranes based on cellulose and cellulose derivatives, in particular cellulose hydrate membranes, or polyethylene membranes are used.

In this case, depending on the solution to be purified, known (polymer) membranes with different pore sizes can be used as starting membranes. According to the invention, for example, a cellulose ester membrane with a pore size of 0.1 to 20 μm, preferably 0.5 to 15 μm and more preferably 1 to 10 μm can be used as a starting membrane that can be saponified and optionally crosslinked by common methods known in the art. The pore size is ordinarily determined by means of a capillary flow porometry test using a Coulter Capillary Flow Porometer 6.0 and the CAPWIN software systems from the firm Porous Materials Inc.

Examples of polymer gels that can be used as a material for the polymeric carrier material of the adsorption medium according to the invention include agarose, dextran, cellulose, polymethacrylates, polyvinyl ethers, polyacrylamides, polystyrene-divinylbenzene copolymers, silica dextran, agarose acrylamides and dextran acrylamides.

Examples of films and wovens include films and wovens composed of the above-mentioned polymer materials that can be used for the (polymer) membranes. Examples of nonwovens that can be used as a material for the polymeric carrier material of the adsorption medium according to the invention include polyester/polypropylene/polyamide nonwovens (such as "Pluratexx 2317 S" from the firm Freudenberg) and the above polymer materials that can be used for the (polymer) membranes.

In the adsorption medium according to the invention, polymeric spacer elements are preferably bound to the surface of the carrier material, wherein the binding between the surface of the carrier material and the spacer elements preferably takes place or has taken place via the functional groups (originally present or produced by surface modification) of the chromatography matrix. By means of the polymeric spacer elements, which in the adsorption medium according to the invention serve as binding units between the chromatography matrix and the multimodal ligands, it is advantageously possible to obtain high ligand densities, which allow high binding capacity for small proteins, such as lysozyme, and high salt tolerance.

In this manner, because of the high ligand densities and the multimodal interactions, salt-tolerant media can be produced that show high protein binding capacity even at an elevated salt concentration.

Within the meaning of the present invention, the term "polymeric spacer elements" (abbreviated as "spacers") is understood to refer to polymers that can bind the internal and external substances of the chromatography matrix to the multimodal ligands. There are no particular limitations on the polymeric spacer elements of the present invention, provided that they can be (preferably) chemically, but also physically bound to the surface of the chromatography matrix. In general, the polymeric spacer elements can be selected from the group composed of polyamines, polyalcohols, polythiols, poly(meth)acrylates, poly(meth)acrylamides, poly-N-alkyl(meth)acrylamides and copolymers composed of two or more of the above polymers, copolymers composed of one or more of the above polymers and polymers that do not carry any nucleophilic functional groups.

According to a preferred embodiment, the polymeric spacer elements are polyamines with at least one primary amino group, as this obviates the need for further functionalization of the surface of the polymeric carrier material for the further reaction. By means of the primary amino group, an amide bond to the multifunctional ligands is later formed as an X—(C=O) bond.

Examples of polyamines within the meaning of the present invention include polyallylamine, polyvinylamine, polyethyleneimine (branched or linear), poly(4-aminostyrene), chitosan, poly-L-lysine, poly(N-methylvinylamine), poly(N-methylallylamine) and poly(oleylamine).

In this case, all suitable polyamines can be used. Preferred, however, are polyamines with a molar mass of more than 500 g/mol, in particular 800 to 1,000,000 g/mol. The polymeric spacer elements particularly preferably have a molar mass of 3,000 to 150,000 g/mol, and more preferably 10,000 to 100,000 g/mol.

In a particularly preferred embodiment, the polymeric spacer elements are selected from the group of polyallylamines with a molar mass of 3,000 to 150,000 g/mol, and more preferably 10,000 to 100,000 g/mol. In a further preferred embodiment, the polymeric spacer elements are selected from the group of polyvinylamines with a molar mass of 5,000 to 500,000 g/mol, and more preferably 10,000 to 100,000 g/mol.

According to the invention, polyallylamine, polyvinylamine and/or polyethyleneimine are particularly preferred.

In the adsorption medium according to the invention, the polymeric spacer elements, if present, are bound both to the surface of the chromatography matrix and to the multimodal ligands. Binding to the multimodal ligands takes place via covalent bonding of the —XH groups (of either the chromatography matrix or the spacer elements) to the carbonyl group of a carboxylic acid derivative as a precursor stage with formation of a —X—(C=O) bond, where X=—NR—, —O— or —S— and R=alkyl, alkenyl, aryl, heteroaryl or H. In a particularly preferred embodiment, binding to the multimodal ligands takes place via a secondary amide bond, i.e. via a bond of the type —NH—(C=O).

The ligand density of the multimodal ligands of the adsorption medium according to the invention is preferably at least 25 µmol/ml, preferably 100 µmol/ml, more preferably at least 150 µmol/ml and particularly preferably at least 250 µmol/ml. The ligand density is determined according to the present invention by titration, with details on this being given under method M2 below.

In a particularly preferred embodiment of a polyamine functionalized adsorption medium, the amino group density, which is the ligand density of the polyamine-functionalized adsorption medium, before the multimodal ligands are immobilized is at least 25 µmol/ml, preferably at least 150 µmol/ml, more preferably at least 200 µmol/ml and particularly preferably at least 400 µmol/ml. The amino group density is determined according to the present invention by titration, with details on this being given under method M1 below.

According to the present invention, the multimodal ligands have the following structure:

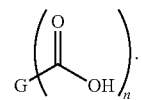

wherein G is preferably selected from the group composed of a branched or unbranched $C_{2-10}$ alkyl group that can contain one or a plurality of heteroatoms selected from O, S, N and halogens, and optionally at least one aromatic substituent, a branched or unbranched $C_{3-10}$ cycloalkyl group that can contain one or a plurality of heteroatoms selected from O, S, N and halogens, and optionally at least one aromatic substituent, a branched or unbranched $C_{2-10}$ alkenyl group that can contain one or a plurality of heteroatoms selected from O, S, N and halogens, and optionally at least one aromatic substituent, a substituted or unsubstituted $C_{6-14}$ aryl group that can contain one or a plurality of heteroatoms selected from O, S, N and halogens, and a substituted or unsubstituted $C_{4-14}$ heteroaryl group that can contain one or a plurality of heteroatoms selected from O, S, N and halogens. The multimodal ligands according to the invention have at least one carboxylic acid group that is bonded to the group G. There is no particular upper limit on the number of carboxylic acid groups, but there should preferably be 5 (n is a whole number from 1 to 5), more preferably 4 (n is a whole number from 1 to 4), and particularly preferably 3 (n is a whole number from 1 to 3).

In a preferred embodiment of the adsorption medium, the multimodal ligands have the following structure:

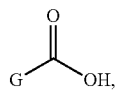

wherein G is a substituted or unsubstituted $C_{2-3}$ alkyl group, a substituted or unsubstituted $C_{3-10}$ cycloalkyl group, a substituted or unsubstituted $C_{2-3}$ alkenyl group, a substituted or unsubstituted $C_6$ aryl group or a substituted or unsubstituted five-membered or six-membered heteroaromatic group, wherein the substituents are selected from the group composed of a branched or unbranched $C_{1-10}$ alkyl group that can contain one or a plurality of heteroatoms selected from O, S, N and halogens, and optionally at least one hydroxyl, carbonyl, carboxyl, carboxylic anhydride or aromatic substituent, a branched or unbranched $C_{2-10}$ alkenyl group that can contain one or a plurality of heteroatoms selected from O, S, N and halogens, and optionally at least one hydroxyl, carbonyl, carboxyl, carboxylic anhydride or aromatic substituent, a $C_{6-20}$ aryl group that can contain one or a plurality of heteroatoms selected from O, S, N and halogens, and optionally at least one hydroxyl, carbonyl, carboxyl, or carboxylic anhydride substituent, a $C_{4-20}$ heteroaryl group that can contain one or a plurality of heteroatoms selected from O, S, N and halogens, and optionally at least one hydroxyl, carbonyl, carboxyl, or carboxylic anhydride substituent, and a hydroxy, thiol or amino group.

In a particularly preferred embodiment of the adsorption medium, G is a branched or unbranched $C_{3-10}$ alkenyl group that can contain one or a plurality of heteroatoms selected from O, S, N and halogens, and optionally at least one hydroxyl, carbonyl, carboxyl, carboxylic anhydride or aromatic substituent.

In a particularly preferred embodiment, the multimodal ligands have one of the following structures:

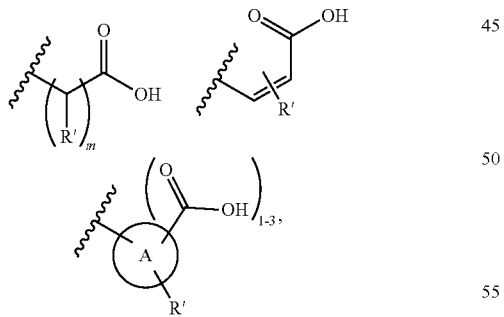

wherein each R' respectively is selected from the group composed of hydrogen, F, Cl, Br, I, —OH, —NH$_2$, SH, CO$_2$H, a branched or unbranched $C_{1-10}$ alkyl group that can contain one or a plurality of heteroatoms selected from O, S, N and halogens, and optionally at least one hydroxyl, carbonyl, carboxyl, carboxylic anhydride or aromatic substituent, a branched or unbranched $C_{2-10}$ alkenyl group that can contain one or a plurality of heteroatoms selected from O, S, N and halogens, and optionally at least one hydroxyl, carbonyl, carboxyl, carboxylic anhydride or aromatic substituent, a $C_{6-20}$ aryl group that can contain one or a plurality of heteroatoms selected from O, S, N and halogens, and optionally at least one hydroxyl, carbonyl, carboxyl, or carboxylic anhydride substituent, and a $C_{4-20}$ heteroaryl group that can contain one or a plurality of heteroatoms selected from O, S, N and halogens, and optionally at least one hydroxyl, carbonyl, carboxyl, or carboxylic anhydride substituent, wherein A is a $C_6$ aryl group or a five-membered or six-membered heteroaromatic group, and wherein m is a whole number from 1 to 3. The multimodal ligand particularly preferably has no further amide bond other than the amide bond via which it can be bonded to the polymeric carrier material.

The following structures (1) through (15) can be mentioned as particularly preferred ligands:

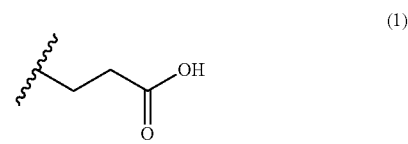

(1)

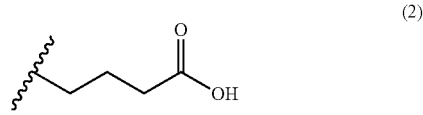

(2)

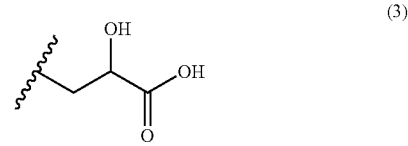

(3)

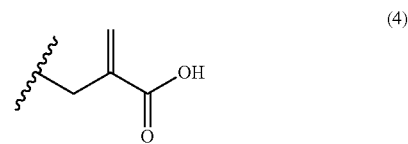

(4)

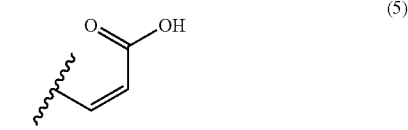

(5)

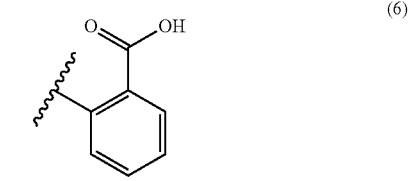

(6)

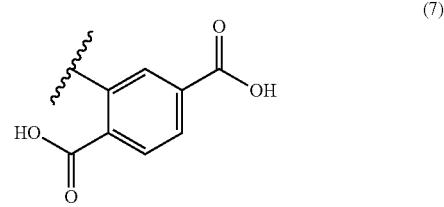

(7)

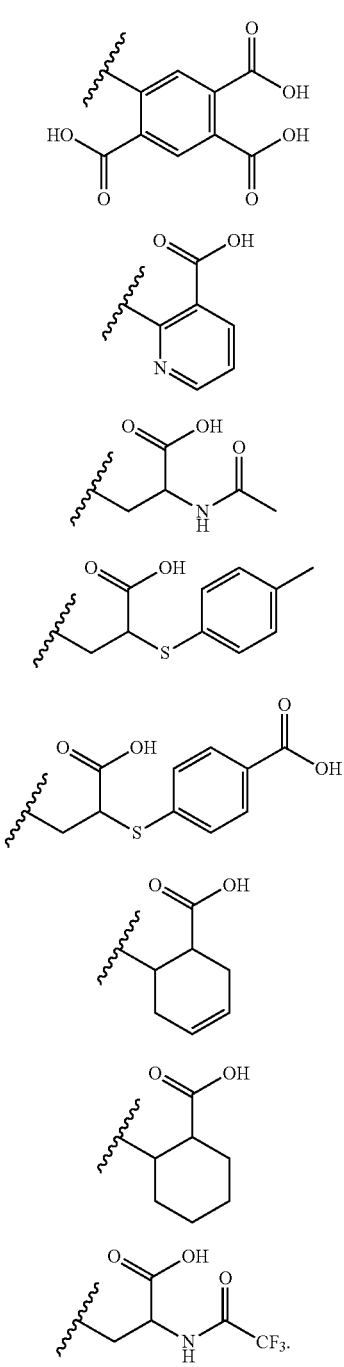

According to the present invention, a multimodal ligand of the following structure is preferably not included in the above general structures for the ligand -G-(CO$_2$H)$_n$:

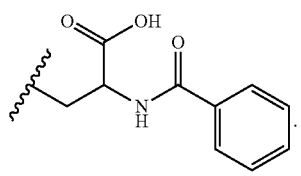 [SMILES: *CC(NC(=O)c1ccccc1)C(=O)O]

Moreover, the present invention provides a method for the production of the adsorption medium according to the invention. The above remarks with respect to the adsorption medium according to the invention therefore also apply to the production method according to the invention.

The method according to the invention for the production of an adsorption medium comprises the following steps:

(a) provision of a polymeric carrier material C, wherein the carrier material C has at least one —XH group that is reactive with carboxylic acid derivatives while forming a covalent bond —X—(C=O), where X denotes —NR—, —O— or —S— and R=alkyl, alkenyl, aryl, heteroaryl or hydrogen; and (b) reaction of the at least one —XH group of the polymeric carrier material C with a carboxylic acid derivative as a precursor of a multimodal ligand such that the covalent bond —X—(C=O) is formed, via which the multimodal ligand is bonded to the carrier material.

In a particularly preferred embodiment of the method according to the invention, the covalent bond —X—(C=O) is a secondary amide bond that is formed by a reaction of a carboxylic anhydride as a precursor of the ligand and amine groups of the carrier material, and the multimodal ligand has at least one free carboxylic acid group.

According to a preferred embodiment, in which the multimodal ligands are bound to the surface of the carrier material via polymeric spacer elements, the polymeric spacer elements are immobilized on the surface of the chromatography matrix before step (b), and the multimodal ligands are then immobilized according to step (b) on the —XH-groups of the spacer elements with formation of an —X—(C=O)— bond, particularly preferably a secondary amide bond.

In step (a) of the method according to the invention, a polymeric carrier material as described above is prepared that originally comprises functional groups (such as polyester fibers) or into which functional groups are introduced by surface modification. Preferably, in a further step (a) of the method according to the invention, polymeric spacer elements are immobilized on the surface of the chromatography matrix, i.e. the spacer elements are (preferably) chemically, or also physically, bound to the surface of the chromatography matrix via their functional groups. There are no particular limitations on the step of immobilization according to the invention, and all immobilization methods known to the person skilled in the art, such as substitution or addition reactions, epoxide opening, aminolysis, amide coupling reactions, esterification, reductive amination and insertion reactions, may be used.

In step (b) of the method according to the invention, the at least one —XH-group, which is optionally immobilized on the carrier material by means of spacer elements, is reacted with a precursor of the multimodal ligands such that a —X—(C=O) bond is formed via which the multimodal ligands are bonded to the carrier material. The —X—(C=O) bond is preferably a secondary amide bond.

According to a preferred embodiment of the present invention, the secondary amide group is formed by reaction of a carboxylic anhydride with amino groups of the carrier material. This means that the amino groups are preferably functionalized with carboxylic anhydrides, as can be illustrated by means of the following diagram:

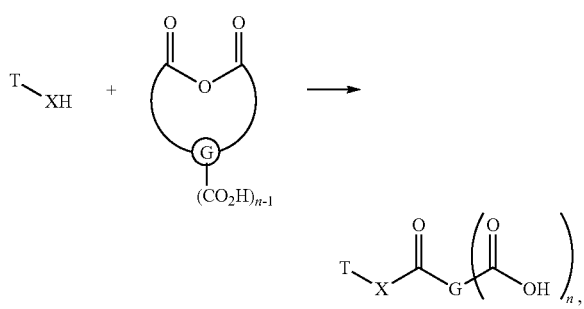

wherein G and n are as defined above and wherein —XH=NH$_2$.

In the G groups which themselves have no carboxylic acid groups —COOH as substituents, the only carboxylic acid group present in the ligand G-(CO$_2$H)$_n$ results from the ring-opening reaction of the carboxylic anhydride with the nucleophilic group —XH, and n is equal to 1.

In the G groups which themselves have at least one carboxylic acid group —COOH as a substituent, n is greater than or equal to 2, wherein one of the carboxylic acid groups results from the ring-opening reaction of the carboxylic anhydride with the nucleophilic group —XH.

According to the invention, there are so particular limitations on the carboxylic anhydride, provided that multimodal ligands of the above structure can be obtained. Examples of suitable carboxylic anhydrides include succinic anhydride, glutaric anhydride, malic anhydride (D- and/or L-isomer), itaconic anhydride, maleic acid anhydride, phthalic anhydride, 1,8-naphthalic anhydride, 1,2,4-benzenetricarboxylic anhydride, quinolinic anhydride, trimellitic anhydride, pyromellitic anhydride, pyridine-3,4-dicarboxylic anhydride, (S)—N-acetyl-L-aspartic anhydride (N-(2,5-dioxotetrahydrofuran-3-yl) acetamide), N-benzoylaspartic anhydride, 3-(p-tolylthio)-succinic anhydride, 4-((2,5-dioxotetrahydrofuran-3-yl)thio)benzoic acid, N-trifluoroacetyl-L-aspartic anhydride (N-(2,5-dioxotetrahydrofuran-3-yl)-2,2,2-trifluoroacetamide), cis-1,2,3,6-tetrahydrophthalic anhydride, 1,2-cyclohexanedicarboxylic anhydride, 2,3-thiophenedicarboxylic anhydride, 3,4-thiophenedicarboxylic anhydride, tetrafluorophthalic anhydride, hexafluoroglutaric anhydride, adipic anhydride, derivatives thereof or mixtures thereof, wherein preferably only one of these substances is used.

As solvents, dimethyl sulfoxide, 2-pyrrolidone, dimethylformamide, dimethylacetamide, tetrahydrofuran or 1,4-dioxane, or other polar, preferably aprotic solvents may be used.

Moreover, the present invention provides use of the adsorption medium according to the invention or an adsorption medium produced according to the method of the invention for the purification of biomolecules. Examples of suitable biomolecules to be purified include proteins, such as antibodies, peptides, amino acids, nucleic acids, virus-like particles, viruses and/or endotoxins.

Because of the polymeric spacer elements, which serve in the adsorption medium according to the invention as connecting units between the chromatography matrix and the multimodal ligands, it is advantageously possible to achieve high densities of ligands having a high binding capacity in particular for small proteins, such as lysozyme. By means of the high ligand densities and the multimodal interactions, salt-tolerant adsorption media can be produced using the method according to the invention that have high protein binding capacity even at an elevated salt concentration of up to 500 mM (NaCl concentration). By selecting the anhydride, the maximum binding capacity of the cation exchange adsorption media can be selectively adjusted over a broad salt concentration range. Because the multimodal ligand structure is produced using only one reagent, the ratio of carboxylic acid groups to the groups that allow further interactions remains constant on the adsorption medium. For this reason, compared to a modification method with two different ligands, each of which is fixed separately on the adsorption medium, or incomplete reactions, the result of the production process is always reproducible. The adsorption medium according to the invention is therefore outstandingly suited for the purification of biomolecules, for which there is significant industrial demand.

Figure 2:
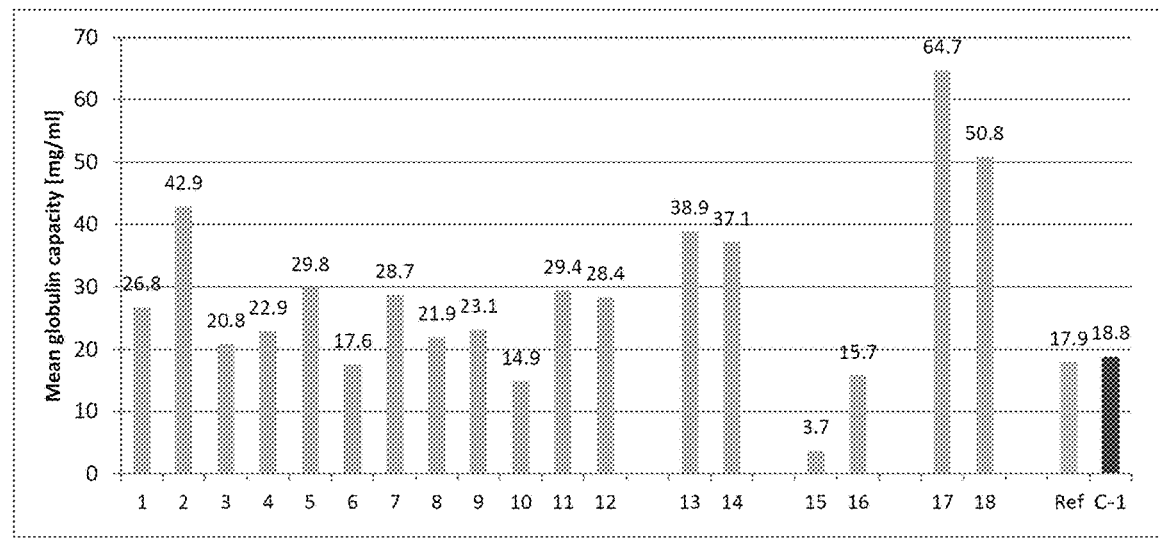
FIG. 2 shows the binding capacity to globulin over a wide salt range for examples 1 to 18, for comparison example 1 (C-1), and for the strong cation exchanger-membrane absorber Sartobind S (Ref) known in the prior art.
Figure 3:
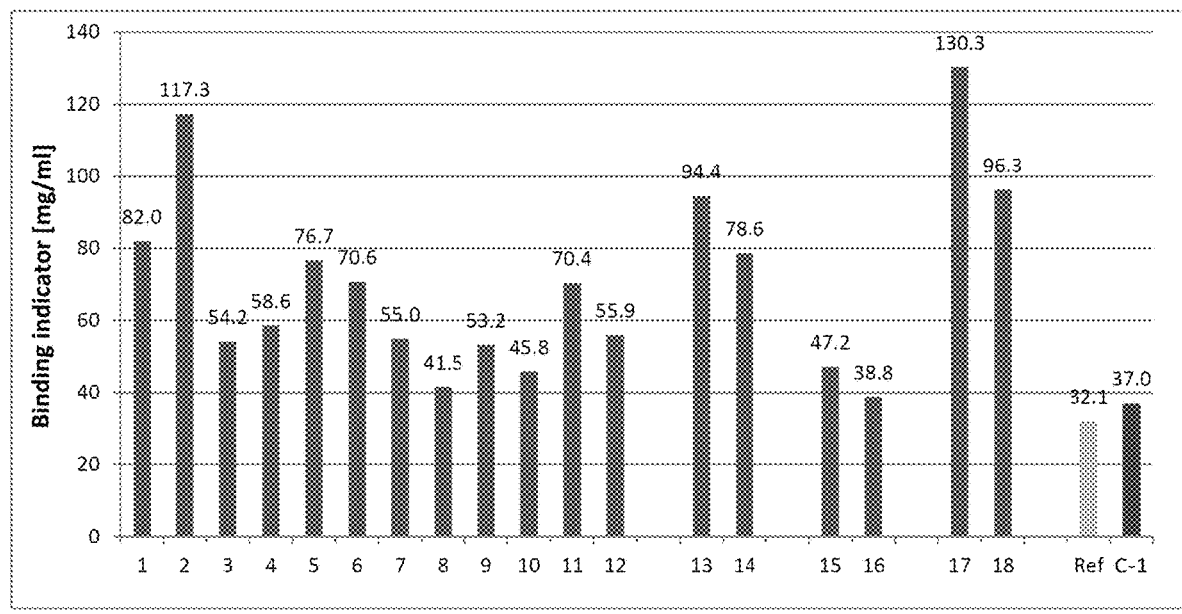
FIG. 3 shows the combined binding capacity to lysozyme and globulin for examples 1-18, for comparison example 1 (C-1), and for the strong cation exchanger-membrane absorber Sartobind S (Ref) known in the prior art.

The present invention will be explained in greater detail by means of the following non-limitative examples, wherein the diagrams shown in FIGS. 1 through 3 summarize the binding capacities of the membranes obtained.

EXAMPLES

Methods

M1: Determination of Ligand/Charge Density of Amine-Functionalized Adsorption Media Three membrane layers were clamped into a membrane holder. The membrane stack had a membrane area of 15 cm$^2$, an inflow area of 5 cm$^2$ and a bed height (thickness of the membrane stack) of 750 μm in the membrane holder. The membranes in the membrane holder were flooded with 20 mM TRIS/HCl buffer at pH=7.4 in order to displace the air and then connected to an Äkta Explorer 100 FPLC unit from the firm General Electric Health Care. The membranes or the membrane stack were then tested for charge density using a test program comprising four steps. The four steps of the test program are given below:
1. conditioning of the membrane with 6 ml of 1 M NaCl solution in 20 mM TRIS/HCl at pH=7.4
2. regeneration of the membrane with 6 ml of a 1 M solution of NaOH in RO water
3. washing of the membrane with 100 ml of RO water and
4. loading of the membrane with 135 ml of 10 mM HCl.

All of the steps were carried out with a flow rate of 10 mL/min. In all of the steps, conductivity was measured in the detector behind the membrane unit. The area above the curve thus recorded was integrated after subtracting the dead volume, and the charge density was calculated therefrom.

M2: Determination of Ligand/Charge Density of Cation Exchange Adsorption Media

Three membrane layers were clamped into a membrane holder. The membrane stack had a membrane area of 15 cm$^2$, an inflow area of 5 cm$^2$ and a bed height (thickness of the membrane stack) of 750 μm in the membrane holder. The membranes in the membrane holder were flooded with 20 mM KPi-Puffer at pH=7 in order to displace the air and then connected to an Äkta Explorer 100 FPLC unit from the firm General Electric Health Care. The membranes or the membrane stack were then tested for charge density using a test program comprising four steps. The four steps of the test program are given below:
1. conditioning of the membrane with 6 ml of 1 M NaCl solution in 20 mM KPi at pH=7.0

2. regeneration of the membrane with 6 ml of a 1 M solution of HCl in RO water
3. washing of the membrane with 88 ml of RO water and
4. loading of the membrane with 135 ml of 10 mM NaOH.

All of the steps were carried out with a flow rate of 10 mL/min. In all of the steps, conductivity was measured in the detector behind the membrane unit. The area above the curve thus recorded was integrated after subtracting the dead volume, and the charge density was calculated therefrom.

M3: Determination of Binding Capacity for Lysozyme of Modified Membranes by Means of Breakthrough Curve Three membrane layers were clamped into a membrane holder. The membrane stack had a membrane area of 15 cm$^2$, an inflow area of 5 cm$^2$ and a bed height (thickness of the membrane stack) of 900 µm in the membrane holder. The membranes in the membrane holder were flooded with 10 mM KPi-Puffer at pH=7 in order to displace the air and then connected to an Äkta Explorer 100 FPLC unit from the firm General Electric Health Care. The membranes or the membrane stack were then tested with a test program comprising three steps with respect to lysozyme-binding capacity. The three steps of the test program are given below:
1. conditioning of the membrane with 20 ml of 1 M NaCl solution in 10 mM KPi at pH=7.0
2. equilibration of the membrane with 20 ml of binding buffer (10 mM KPi, pH=7.0)
3. loading of the membrane with 250 ml of lysozyme solution (0.20% lysozyme in binding buffer).

All of the steps were carried out with a flow rate of 10 mL/min. In all of the steps, absorption at 280 nm was measured in the detector behind the membrane unit. The area above the curve thus recorded was integrated after subtracting the dead volume, and the amount of bound lysozyme was calculated therefrom.

M4: Determination of Binding Capacity for γ-Globulin of Modified Membranes by Means of Breakthrough Curve Three membrane layers were clamped into a membrane holder. The membrane stack had a membrane area of 15 cm$^2$, an inflow area of 5 cm$^2$ and a bed height (thickness of the membrane stack) of 900 µm in the membrane holder. The membranes in the membrane holder were flooded with 20 mM NaAc solution at pH=5 in order to displace the air and then connected to an Äkta Explorer 100 FPLC unit from the firm General Electric Health Care. The membranes or the membrane stack were then tested with a test program comprising three steps with respect to γ-globulin-binding capacity. The three steps of the test program are given below:
1. conditioning of the membrane with 20 ml of 1 M NaCl solution in 20 mM NaAc at pH=5.0
2. equilibration of the membrane with 20 ml of binding buffer (25 mM NaCl in 20 mM NaAc at pH=5.0)
3. loading of the membrane with 250 ml of 1 mg/mL γ-globulin solution in binding buffer.

All of the steps were carried out with a flow rate of 10 mL/min. In all of the steps, absorption at 280 nm was measured in the detector behind the membrane unit. The area above the curve thus recorded was integrated after subtracting the dead volume, and the amount of bound γ-globulin was calculated therefrom. The measurement was repeated using a fresh membrane sample with 150 mM NaCl and 300 mM NaCl.

Modification Protocol for the Immobilization of Carboxylic Anhydrides on Amine-Modified Starting Matrices

Modification of Cellulose Hydrate Membranes

1. Polyamine Immobilization

1a) Polyallylamine (PAA)

The spacer immobilization is based on a known protocol, which was described in DE 10 2008055 821 A1 (examples 21 and 22). In this case, spacers with a molar mass of 15,000 g/mol to 150,000 g/mol are used. In a typical reaction, the cellulose acetate (CA) membrane (3 µm pore size, Sartorius Stedim Biotech GmbH) was saponified in a 0.6 M aqueous sodium hydroxide solution (4 g/cm$^2$) for 30 min at room temperature and then rinsed three times for 10 min in a 0.25 M sodium hydroxide solution (0.5 g/cm$^2$). The membrane obtained was treated for 30 min with a solution composed of 15% 1,4-butanediol diglycidyl ether and 85% 0.25 M aqueous sodium hydroxide solution (0.5 g/cm$^2$) and then stored for 18 h in a sealed container at room temperature. Finally, rinsing was carried out for 30 min with running water.

The membrane thus obtained was treated for 1 h with a 20% solution of polyallylamine in RO water (1 g/cm$^2$) at 50° C. The membrane was then treated for 5 min at room temperature with 5% sulfuric acid solution and finally rinsed for 10 min with running water.

The amino group density on the membrane was determined by titration.

| Carrier material | Amino group density |
|---|---|
| PAA-modified cellulose hydrate membranes | 450-550 µmol/mL |

1b) Polyethyleneimine (PEI)

Spacer immobilization is carried out based on a known protocol, which was described in DE 102008055 821 A1 (examples 15, 16 and 17). In a typical reaction, the CA membrane (3 µm pore size, Sartorius Stedim Biotech GmbH) was saponified in a 0.6 M aqueous sodium hydroxide solution (4 g/cm$^2$) for 30 min at room temperature and then rinsed three times for 10 min in a 0.25 M sodium hydroxide solution (0.5 g/cm$^2$). The membrane obtained was treated for 30 min with a solution composed of 15% 1,4-butanediol diglycidyl ether and 85% 0.25 M aqueous sodium hydroxide solution (0.5 g/cm$^2$) and then stored for 18 h in a sealed container at room temperature. Finally, rinsing was carried out for 30 min with running water. The membrane thus obtained was treated for 2 h with a 30% solution of Lupasol WF (polyethyleneimine from BASF AG, molecular mass 25000 g/mol) in RO water (1 g/cm$^2$) at 50° C. The membrane was then rinsed for 30 min with running water, treated for 10 min with 5% sulfuric acid solution, and finally rinsed for 10 min with running water.

The amino group density on the membrane was determined by titration.

| Carrier material | Amino group density |
|---|---|
| PEI-modified cellulose hydrate membranes | 600-650 µmol/mL |

2. Ligand Immobilization

In a typical reaction, 16 g of carboxylic anhydride was dissolved in 64 g of DMSO (20 wt %) and the solution was heated to 60° C. The PAA-modified cellulose hydrate membrane was placed in the reaction solution (0.5 g/cm²) and agitated at 60° C. for 1 h. The reaction solution was then filtered off, and the membrane was washed with ethanol (0.5 g/cm²) and a large excess of RO water.

Ligand Structures:

The cation exchangers listed here were produced according to the above-described method, wherein the following carboxylic anhydrides were used. The results are shown in Tables 1 through 3 and FIGS. 1 through 3 below.

| Example | Anhydride |
|---|---|
| 1 | Succinic anhydride |
| 2 | Glutaric anhydride |
| 3 | Malic anhydride |
| 4 | Itaconic anhydride |
| 5 | Maleic anhydride |
| 6 | Phthalic anhydride |
| 7 | Quinolinic anhydride |
| 8 | Trimellitic anhydride |
| 9 | Pyromellitic anhydride |
| 10 | 4-((2,5-dioxotetrahydrofuran-3-yl)thio)benzoic acid |
| 11 | N-(2,5-dioxotetrahydrofuran-3-yl)acetamide |
| 12 | N-(2,5-dioxotetrahydrofuran-3-yl)-2,2,2-trifluoroacetamide |
| 13 | Maleic anhydride |
| 14 | Maleic anhydride |
| 15 | Succinic anhydride |
| 16 | Maleic anhydride |
| C-1* | N-benzoyl-L-aspartic anhydride |

*Comparison example 1

As a comparison, a strong cation exchanger-membrane adsorber known in the prior art, Sartobind S (strong cation exchanger of cellulose hydrate with sulfonic acid ligands, Sartorius Stedim Biotech GmbH), was tested. The results are marked with "Ref" in Table 4 and FIGS. 1 through 3 below.

Moreover, a reaction of N-benzoyl-L-aspartic anhydride with the PAA-modified cellulose hydrate membrane (molar mass of PAA: 15,000 g/mol) was carried out as comparison example 1, thus obtaining a chromatography matrix with a 2-(benzoylamino) butanoic acid ligand in order to recreate the Capto™ MMC ligands known from prior art.

TABLE 1

Polyallylamine spacers (M = 15,000 g/mol)

| | Poly-amine | Structure | Capacity, lysozyme [mg/mL] $^{M3}$ | Capacity, globulin 25 mM NaCl [mg/mL] $^{M4}$ | Capacity, globulin 150 mM NaCl [mg/mL] $^{M4}$ | Capacity, globulin 300 mM NaCl [mg/mL] $^{M4}$ | Ligand density, polyamine-functionalized membrane [µmol/mL] $^{M1}$ | Ligand density, anhydride-functionalized membrane [µmol/mL] $^{M2}$ |
|---|---|---|---|---|---|---|---|---|
| 1 | PAA (15,000 g/mol) | 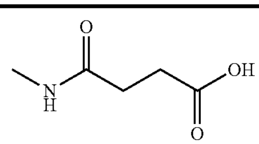 | 137.1 | 60.0 | 20.0 | 0.3 | 494 | 431 |
| 2 | PAA (15,000 g/mol) | 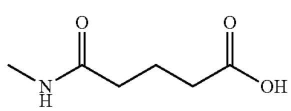 | 191.7 | 97.2 | 30.6 | 0.8 | 494 | 438 |
| 3 | PAA (15,000 g/mol) | 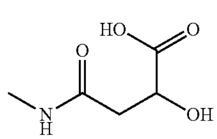 | 87.5 | 31.3 | 21.9 | 9.4 | 494 | 290 |
| 4 | PAA (15,000 g/mol) | 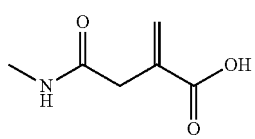 | 94.3 | 22.9 | 31.4 | 14.3 | 550 | 574 |
| 5 | PAA (15,000 g/mol) | 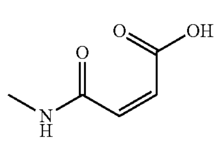 | 123.5 | 23.5 | 42.4 | 23.5 | 494 | 441 |

TABLE 1-continued

| | Poly-amine | Structure | Capacity, lysozyme [mg/mL] [M3] | Capacity, globulin 25 mM NaCl [mg/mL] [M4] | Capacity, globulin 150 mM NaCl [mg/mL] [M4] | Capacity, globulin 300 mM NaCl [mg/mL] [M4] | Ligand density, polyamine-functionalized membrane [μmol/mL] [M1] | Ligand density, anhydride-functionalized membrane [μmol/mL] [M2] |
|---|---|---|---|---|---|---|---|---|
| 6 | PAA (15,000 g/mol) | | 123.7 | 15.0 | 15.7 | 22.0 | 524 | 525 |
| 7 | PAA (15,000 g/mol) | | 81.2 | 29.7 | 37.1 | 19.4 | 494 | 425 |
| 8 | PAA (15,000 g/mol) | | 61.1 | 16.0 | 24.5 | 25.3 | 494 | 760 |
| 9 | PAA (15,000 g/mol) | | 83.3 | 16.7 | 30.6 | 22.2 | 494 | 833 |
| 10 | PAA (15,000 g/mol) | | 76.8 | 13.0 | 13.3 | 18.3 | 546 | 640 |
| 11 | PAA (15,000 g/mol) | | 111.4 | 57.1 | 14.3 | 16.9 | 546 | 437 |
| 12 | PAA (15,000 g/mol) | | 83.4 | 39.1 | 40.7 | 5.4 | 546 | 534 |

TABLE 1-continued

Polyallylamine spacers (M = 15,000 g/mol)

| Poly-amine | Structure | Capacity, lysozyme [mg/mL] $^{M3}$ | Capacity, globulin 25 mM NaCl [mg/mL] $^{M4}$ | Capacity, globulin 150 mM NaCl [mg/mL] $^{M4}$ | Capacity, globulin 300 mM NaCl [mg/mL] $^{M4}$ | Ligand density, polyamine-functionalized membrane [μmol/mL] $^{M1}$ | Ligand density, anhydride-functionalized membrane [μmol/mL] $^{M2}$ |
|---|---|---|---|---|---|---|---|
| C-1* | PAA (15,000 g/mol) | | 55.3 | 15.3 | 17.1 | 24.0 | 494 | 473 |

*Comparison example 1

TABLE 2

Polyallylamine spacers (M = 100,000 g/mol and 150,000 g/mol)

| | Polyamine | Structure | Capacity, lysozyme [mg/mL] $^{M3}$ | Capacity, globulin 25 mM NaCl [mg/mL] $^{M4}$ | Capacity, globulin 150 mM NaCl [mg/mL] $^{M4}$ | Capacity, globulin 300 mM NaCl [mg/mL] $^{M4}$ | Ligand density, polyamine-functionalized membrane [μmol/mL] $^{M1}$ | Ligand density, anhydride-functionalized membrane [μmol/mL] $^{M2}$ |
|---|---|---|---|---|---|---|---|---|
| 13 | PAA (150,000 g/mol) | 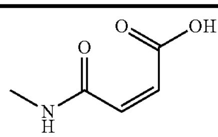 | 150.0 | 26.7 | 56.7 | 33.3 | 843 | 506 |
| 14 | PAA (100,000 g/mol) | 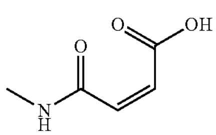 | 120.0 | 31.4 | 54.3 | 25.7 | 667 | 345 |

TABLE 3

Polyethyleneamine spacers (M = 25,000 g/mol)

| | Polyamine | Structure | Capacity, lysozyme [mg/mL] $^{M3}$ | Capacity, globulin 25 mM NaCl [mg/mL] $^{M4}$ | Capacity, globulin 150 mM NaCl [mg/mL] $^{M4}$ | Capacity, globulin 300 mM NaCl [mg/mL] $^{M4}$ | Ligand density, polyethyleneimine-functionalized membrane [μmol/mL] $^{M1}$ | Ligand density, anhydride-functionalized membrane [μmol/mL] $^{M2}$ |
|---|---|---|---|---|---|---|---|---|
| 15 | PEI (25,000 g/mol) | 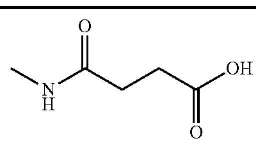 | 90.7 | 6.7 | 3.3 | 1.1 | 650 | 373 |
| 16 | PEI (25,000 g/mol) | 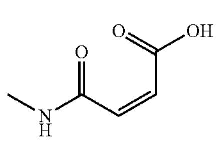 | 61.9 | 35.5 | 9.7 | 2.1 | 650 | 548 |

TABLE 4

| | Structure | Capacity, lysozyme [mg/mL] $^{M3}$ | Capacity, globulin 25 mM NaCl [mg/mL] $^{M4}$ | Capacity, globulin 150 mM NaCl [mg/mL] $^{M4}$ | Capacity, globulin 300 mM NaCl [mg/mL] $^{M4}$ | Ligand density, [µmol/mL] $^{M2}$ |
|---|---|---|---|---|---|---|
| Ref | Sartobind S | 46 | 37 | 14 | 2 | 96 |

Modification of Polyethylene Membranes

1. Ligand Immobilization

The polyallylamine-functionalized polyethylene membrane Chromasorb (0.65 µm pore size, EMD Millipore) was used as a starting material for ligand immobilization. In a typical reaction, 16 g of carboxylic anhydride was dissolved in 64 g of DMSO (20 wt %) and the solution was heated to 60° C. The polyallylamine-functionalized polyethylene membrane was placed in the reaction solution (0.5 g/cm²) and agitated at 60° C. for 1 h. The reaction solution was then filtered off, and the membrane was washed with ethanol (0.5 g/cm²) and a large excess of RO water.

The cation exchangers listed here were produced according to the above-described method, wherein the following carboxylic anhydrides were used. The results are shown in Table 5 below.

| Example | Anhydride |
|---|---|
| 17 | Succinic anhydride |
| 18 | Maleic anhydride |

In addition, all of the examples show favorable binding properties for larger molecules, such as globulin, over a wide salt range (25 mM to 300 mM NaCl). In order to better describe this binding capacity, a mean binding capacity is defined for globulin $\overline{BC}$ (globulin):

$$\overline{BC}(\text{globulin}) = \frac{BG(\text{globulin, 25 mM NaCl}) + BC(\text{globulin, 150 nM NaCl}) + BC(\text{globulin, 300 mM NaCl})}{3}$$

The results are summarized in FIG. 2.

In order to allow determination of a result with respect to the performance of the individual examples for numerous applications, the binding capacity for both small molecules (lysozyme) and large molecules (globulin) is taken into account below. For this purpose, a binding indicator $\overline{BC}$ (total) is defined:

$$\overline{BC}(\text{total}) = \frac{BC(\text{lysozyme}) + \overline{BC}(\text{globulin})}{2}$$

The results are summarized in FIG. 3. Surprisingly, the membranes according to the invention show a significantly higher binding indicator $\overline{BC}$ (total) compared to the membrane obtained in comparison example 1. The same applies for the strong cation exchanger-membrane adsorber Sartobind S known in the prior art.

The invention claimed is:

1. A multimodal adsorption medium having a functional surface, comprising a polymeric carrier material with polymeric spacer elements bound to the surface thereof, to which

TABLE 5

| | Structure | Capacity, lysozyme [mg/mL] $^{M3}$ | Capacity, globulin 25 mM NaCl [mg/mL] $^{M4}$ | Capacity, globulin 150 mM NaCl [mg/mL] $^{M4}$ | Capacity, globulin 300 mM NaCl [mg/mL] $^{M4}$ | Ligand density, polyamine-functionalized membrane [µmol/mL] $^{M1}$ | Ligand density, anhydride-functionalized membrane [µmol/mL] $^{M2}$ |
|---|---|---|---|---|---|---|---|
| 17 | (structure: methylamide-succinic acid) | 195.8 | 132.5 | 58.3 | 3.3 | 858 | 533 |
| 18 | (structure: methylamide-maleic acid) | 141.7 | 47.5 | 71.7 | 33.3 | 858 | 500 |

Evaluation of Results

The results are summarized in FIGS. 1 through 3. As shown in FIG. 1, compared to the membrane obtained in comparison example 1, the membranes according to the invention with the multimodal ligands surprisingly show significantly higher binding capacity to small molecules, such as lysozyme, at comparable ligand density. The same applies for the strong cation exchanger-membrane adsorber Sartobind S known in the prior art.

multimodal ligands of the following structure -G-(CO₂H)$_n$ are covalently bonded via an —X—(C=O) group,

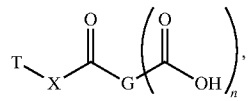

where T denotes the polymeric carrier material with the polymeric spacer elements bound to the surface thereof, X denotes an —NH— moiety on the polymeric spacer element, the structure -G-(CO$_2$H)$_n$ is selected from the group consisting of (3), (4), (6) to (14) and (15):

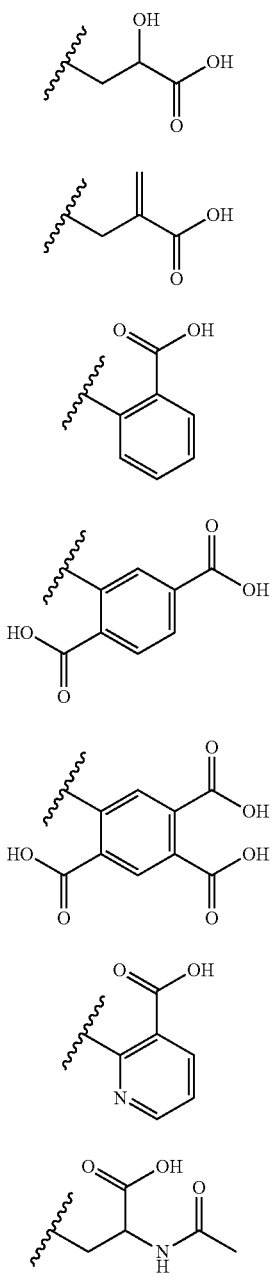

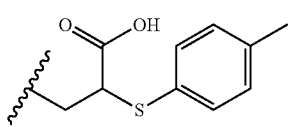

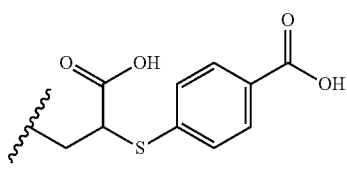

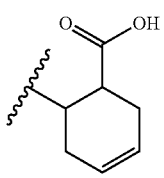

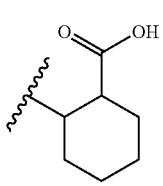

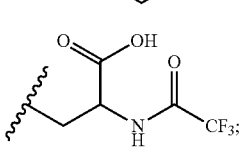

and
wherein the polymeric spacer elements are selected from the group consisting of polyallylamine, polyvinyladine, poly(4-aminostyrene), poly-L-lysine, poly(N-methylvinylamine), poly(N-methylallylamine) and poly(oleylamine).

2. The multimodal adsorption medium as claimed in claim 1, wherein the polymeric carrier material comprises at least one material selected from the group consisting of natural or synthetic fibers, (polymer) membranes, porous, polymeric monolithic molded bodies, polymer gels, films, nonwovens and wovens.

3. The multimodal adsorption medium as claimed in claim 1, wherein the polymeric spacer elements comprises at least one primary amino group, which as an X—(C=O) bond forms an amide bond with the multimodal ligands.

4. The multimodal adsorption medium as claimed in claim 3, wherein the polymeric spacer has a molar mass of more than 500 g/mol.

5. The multimodal adsorption medium as claimed in claim 1, wherein the polymeric spacer elements are selected from the group of polyallylamines with a molar mass of 3,000 to 150,000 g/mol.

6. The multimodal adsorption medium as claimed in claim 1, wherein the ligand density of the multimodal ligands of the adsorption medium is at least 25 μmol/ml.

* * * * *